United States Patent
Bernard

(10) Patent No.: US 6,676,625 B2
(45) Date of Patent: Jan. 13, 2004

(54) DESIGNER TAMPON APPLICATOR PLUNGER AND WITHDRAWAL STRING

(76) Inventor: Joella M Bernard, 130 E. San Fernando St., PH#17, San Jose, CA (US) 95112

( * ) Notice: Subject to any disclaimer, the term of this patent is extended or adjusted under 35 U.S.C. 154(b) by 0 days.

(21) Appl. No.: 09/875,672

(22) Filed: Jun. 5, 2001

(65) Prior Publication Data

US 2002/0183681 A1 Dec. 5, 2002

(51) Int. Cl.$^7$ ................................................ A61F 13/20
(52) U.S. Cl. ........................................................ 604/15
(58) Field of Search ............................. 604/11–18, 904

(56) References Cited

U.S. PATENT DOCUMENTS

| | | | | |
|---|---|---|---|---|
| 1,555,708 A | * | 9/1925 | Gale | ............................ 604/904 |
| 3,037,506 A | * | 6/1962 | Penksa | ........................ 604/904 |
| 3,863,636 A | | 2/1975 | Johnson | |
| 3,948,257 A | | 4/1976 | Bossak | |
| 4,276,881 A | | 7/1981 | Lilaonitkul | |
| 4,332,251 A | * | 6/1982 | Thompson | .................... 604/15 |
| 4,650,459 A | | 3/1987 | Sheldon | |
| 5,004,106 A | | 4/1991 | Blumstock et al. | |
| 5,338,586 A | * | 8/1994 | Chalfin | ......................... 428/28 |
| 5,395,308 A | | 3/1995 | Fox et al. | |
| 5,569,177 A | | 10/1996 | Fox et al. | |
| 5,674,239 A | * | 10/1997 | Zadini et al. | ................. 604/904 |
| 5,709,652 A | | 1/1998 | Hagerty | |
| 5,730,294 A | | 3/1998 | Blosser et al. | |
| 5,755,706 A | * | 5/1998 | Kronenthal et al. | ......... 604/904 |
| 5,840,055 A | * | 11/1998 | Sgro | ............................. 604/11 |
| 5,873,971 A | | 2/1999 | Balzar | |
| 6,017,321 A | | 1/2000 | Boone | |
| 6,036,666 A | | 3/2000 | Peiler et al. | |
| 6,039,175 A | | 3/2000 | Wright | |
| 6,142,984 A | | 11/2000 | Brown et al. | |
| 6,312,419 B1 | * | 11/2001 | Durel-Crain | |

OTHER PUBLICATIONS

Crutchley A., "Fassel Making" (2000) (Southwater Imprint of Anness Publishing Inc. New York N.Y.).

* cited by examiner

*Primary Examiner*—Dennis Ruhl
(74) *Attorney, Agent, or Firm*—Intellectual Property Law Group LLP; Otto O. Lee; Juneko Jackson

(57) ABSTRACT

A designer tampon applicator, plunger and withdrawal string is disclosed. The disclosed invention decreases the embarrassment and removes the stigma of menstruation by converting a feminine hygiene product requiring maximum discretion into a high-fashion accessory suitable for public display and personal or intimate adornment. The disclosed invention also allows use of a larger tampon pledget providing greater absorption of and a more effective barrier to menstrual flow. Furthermore, the designer withdrawal string provides a highly visible reminder a tampon is in place and very effective means of removing the tampon.

12 Claims, 1 Drawing Sheet

DESIGNER TAMPON APPLICATOR PLUNGER AND WITHDRAWAL STRING

BACKGROUND

This invention relates generally to tampon applicators, and specifically relates to designer tampon applicators and withdrawal strings.

The catamenial tampon to absorb and obstruct the flow of menses is a well-known product for personal feminine hygiene. There are three general types of tampons: plunger, stick and digital, with plunger being the most prevalent type in the United States. Plunger tampons are generally formed of two telescoping tubes: an outer tube or applicator containing the tampon pledget and an inner tube or plunger used to expel the pledget. A withdrawal string, which passes through the plunger, is attached to the pledget. Typical of the art are the tampon applicator as disclosed in U.S. Pat. No. 5,569,177 issued to Fox and the tampon pledget as disclosed in U.S. Pat. No. 5,873,971 issued to Balzar. Plunger tampons should possess necessary attributes of absorbency, comfort, physical protection and psychological support.

Great effort has been expended in developing plunger tampons which are easy and comfortable to insert, swell to obstruct the vaginal canal and absorb menses, are easy and comfortable to withdraw, and are readily disposable. A plastic applicator with a "pattern" of grooves to facilitate accelerated breakup when immersed in water is described in U.S. Pat. No. 5,395,308 issued to Fox. While the pattern of grooves may be visually pleasing, the effect is incidental to the purpose.

Psychological support for the menstruating women has been limited to issues of comfort, protection, discretion and deodorization. Protection and discretion are to some degree antagonistic. Protection dictates a larger tampon delivering a more adequate barrier and increased absorption, whereas discretion dictates a smaller tampon that is more easily hidden and possesses decreased barrier and absorptive properties. A "floral petal" deodorant tag suspended at the mid-point of the withdrawal string is described in U.S. Pat. No. 3,948,257 issued to Bossak. Here the decorative value is incidental to the purpose of providing a vehicle to deliver deodorant.

Comparatively little effort has been expended on making the withdrawal string that is easy to find, easy to grip, attractive and intentionally conspicuous after insertion. The increased comfort of tampons demands a conspicuous withdrawal string to prevent the tampon from being accidentally left in place. Yet, the withdrawal string is considered an item of discomfort and embarrassment, which the user does not want to feel, see or have inadvertently revealed. Revealing the withdrawal string at the periphery of swimwear, sportswear, underwear or other clothing, even during intimacy, is considered a major embarrassment. A tampon with internally packed "colored" withdrawal string contrasting with the tampon pledget is described in U.S. Pat. No. 3,863,636 issued to Johnson. Here the purpose of a string color contrasting with the tampon pledget is to facilitate the user finding the string before insertion of the tampon rather than assisting the user to find the withdrawal string at the time of removal. There is no intent for the "colored" string to be for public display or personal adornment. A reminder sticker to alert the user a tampon is in place is described in U.S. Pat. No. 6,017,321 issued to Boone. However, this patent does not contemplate the reminder sticker to be attached to the withdrawal string while the tampon is inserted, as it claims to solve the problem of reminding users "about tampons in use without the intrusiveness of the tag device of Bossak". A "textured non-wicking" withdrawal string is described in U.S. Pat. No. 6,142,984 issued to Brown. Here the principle purpose of texturing the withdrawal string is to provide grippability without increasing diameter and consequently causing the user to notice or feel the string when the tampon is in place. Again, there is no intent for the textured string to be for public display or personal or intimate adornment.

Although sexually mature females, unless pregnant, typically menstruate one week in four throughout their reproductive lives, menstruation and associated feminine hygiene products are still, even in these enlightened times, considered a major source of embarrassment and stigmatization. While a necessity for sexually mature females, tampon applicators and plungers are not considered suitable items for public display. Similarly, neither is a tampon withdrawal string considered a suitable item for personal or intimate adornment. The degree of embarrassment associated with the use of catamenial tampons is evidenced by the effort to make the tampons smaller, easier to hide, and thus more discrete. This embarrassment is emphasized by prior art in which decorative wallets, containers and cases are described to discreetly hide tampons from public view. Typical of the art of camouflage are U.S. Pat. No. 5,004,106 issued to Blumstock, U.S. Pat. No. 5,730,294 issued to Blosser and U.S. Pat. No. 6,039,175 issued to Wright. Tampons should be seen as a liberating invention yet they are forced to take a discrete place in the bottom of purses and in grocery or drug store aisles labeled "feminine protection."

An important object of the current invention is to remove the embarrassment and stigma associated with menstruation. Removal of embarrassment and stigma is accomplished by eliminating any need for discretion when using tampons. Removing embarrassment and stigma will raise the morale of the user. Raising the morale of the user is vitally important at a time in the month when morale may be at its lowest due to bloating, cramping and mood swings resulting from hormonal changes. Raising the morale of the user is also vitally important at time of the month when opportunities for intimacy have been limited. Menstruation, an indication of a woman's health and fertility, should not be an embarrassing misery to be publicly stigmatized and suffered in private. Instead, menstruation should be amenable to celebration through fashionable display and personal or intimate adornment. A tampon should be as suitable for public display as any other fashion accessory. A tampon should provide the same degree of personal adornment and private pleasure as any other item of intimate apparel.

An additional object of the present invention is to provide an intentionally decorated high-fashion designer tampon applicator and plunger which is not limited in size by the need to be hidden for discretion and thus capable of delivering a larger tampon pledget providing a more adequate barrier and increased absorption of menstrual flow.

Another object of the present invention is to provide an intentionally decorated high-fashion designer tampon applicator and plunger that will encourage more frequent changes of the tampon pledget. Frequent change of the tampon pledget decreases the risk of Toxic Shock Syndrome (TSS), a serious life-threatening infection.

It is also the object of the present invention to provide an intentionally decorated high-fashion designer tampon applicator and plunger capable of improving effectiveness where a tampon is used for contraceptive, diagnostic or therapeutic purposes.

Still another object of the present invention is to provide an intentionally decorated high-fashion designer withdrawal string, suitable for both public display and personal or intimate adornment to eliminate the embarrassment and stigma associated with female hygiene products and thus able to raise the morale of the user during menstruation.

Yet another object of the present invention is to provide an intentionally decorated high-fashion designer withdrawal string, suitable for personal or intimate adornment and capable of providing highly visible reminder a tampon pledget is in place. Inadvertently leaving a tampon pledget in place in the vaginal canal may lead to Toxic Shock Syndrome (TSS), a serious life-threatening infection.

A further object of the present invention is to provide an intentionally decorated high-fashion designer withdrawal string, suitable for personal or intimate adornment with an adequate diameter, length and end-stop to obtain the grip necessary to provide a more adequate pull for removing the tampon pledget.

Yet another object of the present invention is to provide an intentionally decorated high-fashion designer withdrawal string, suitable for personal or intimate adornment capable of improving compliance where a tampon is used for contraceptive, diagnostic or therapeutic purposes.

SUMMARY

The aesthetic appearance of the tampon applicator, plunger and withdrawal string is improved by intentional application of the decorative arts, making the ensemble a high-fashion designer accessory in addition to being a feminine hygiene product. Once the tampon pledget is inserted into the vaginal canal, the withdrawal string becomes an intentional item of personal or intimate adornment in addition to being a functional means of detection and removal.

Making the tampon applicator, plunger and withdrawal string intentionally visible high-fashion accessories and the withdrawal string an item of personal or intimate adornment eliminates any need for discretion. Eliminating the need for discretion frees the user from embarrassment and consequently raises their morale. As a high-fashion accessory, the designer tampon applicator, plunger and withdrawal string become a suitable item for public display. This encourages more frequent changes of tampon, decreasing the risk of a life threatening Toxic Shock Syndrome (TSS) infection. By becoming a high-fashion designer good, the tampon moves from being a feminine hygiene product sold in supermarkets and drug stores to being a couture accessory sold in apparel, department, lingerie, sportswear and swimwear stores. The change in retail outlet will also result in improved morale for the user and others who may purchase such designer tampons on their behalf.

By eliminating any need for a reduction in size to facilitate discretion, an intentionally decorated high-fashion designer tampon applicator and plunger can deliver a larger tampon pledget. A larger tampon pledget provides a more adequate barrier to and increased absorption of menstrual flow. The more adequate barrier and increased absorption provide greater security from fear of leakage and thus increased psychological support to the user.

An intentionally decorated withdrawal string, suitable for personal or intimate adornment, makes for a highly visible and deliberately sought out reminder a tampon is in place. Such a highly visible and intentional decoration provides additional security the withdrawal string will not be overlooked and a tampon inadvertently left in place. Inadvertently leaving a tampon pledget in place may lead to Toxic Shock Syndrome (TSS) a serious life-threatening infection. Freedom from fear a tampon will be inadvertently left in place provides an additional dimension of psychological support to the user.

An intentionally decorated withdrawal string, suitable for personal or intimate adornment, also provides the diameter, length and end-stop needed to enhance grip. Enhanced grip is needed to obtain the adequate pull required to remove of the tampon pledget. Certainty of removal provides a further additional dimension of psychological support to the user.

Where the purpose of the tampon is contraceptive, diagnostic or therapeutic, a high-fashion designer applicator, plunger and withdrawal string can be expected to increase compliance. An aesthetically pleasing non-medical high-fashion designer applicator and plunger will encourage use. A designer withdrawal string suitable for personal or intimate adornment will encourage retention where this is required. Catamenial, contraceptive, diagnostic, and therapeutic tampons can be made outwardly indistinguishable. Since the designer tampon is in part fashion accessory, its underlying purpose, whether catamenial, contraceptive, diagnostic or therapeutic, is not revealed either before or during use. In a preferred embodiment, the present invention is a decorated tampon applicator that has an elongated tube designed to hold a tampon pledget, said tube having: an outer surface, and first and second spaced apart ends. The decorated tampon applicator also has a plunger having an outer periphery, said plunger being telescopically mounted in the first end of the tube. The outer surface and the outer periphery includes one or more decorative patterns.

In an alternative embodiment, the present invention is a tampon applicator device that has a tampon pledget, an elongated tube capable of holding the tampon pledget. The tube has an outer surface, and first and second spaced apart ends. The tampon applicator device also has a plunger having an outer periphery, said plunger being telescopically mounted in the first end of the tube, and a tassel member extending from the tampon pledget. This tassel member has a cord member comprising at least one cord, said cord member having a first end and a second end, the first end being attached to the tampon pledget; and a skirt extending from the second end of the cord member.

In yet another preferred embodiment, the present invention is a tampon applicator device of above further comprising a decorative pattern on the outer surface and the outer periphery.

DRAWINGS

These and other features, aspects, and advantages of the present invention will be better understood from the following drawings, description and appended claims, where:

DETAILED DESCRIPTION OF THE INVENTION

Figure 1:
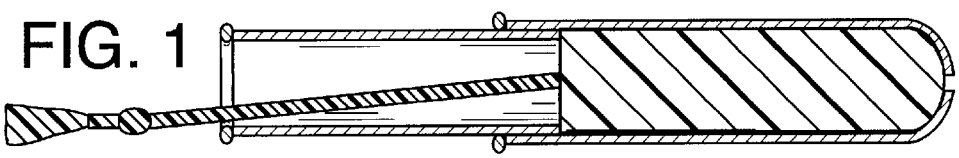
FIG. 1 is a longitudinal section of a plunger type tampon showing an outer tube or applicator containing the tampon pledget, an inner tube or plunger used to expel the pledget and a withdrawal string passing through the plunger and attached to the pledget.
Figure 2:
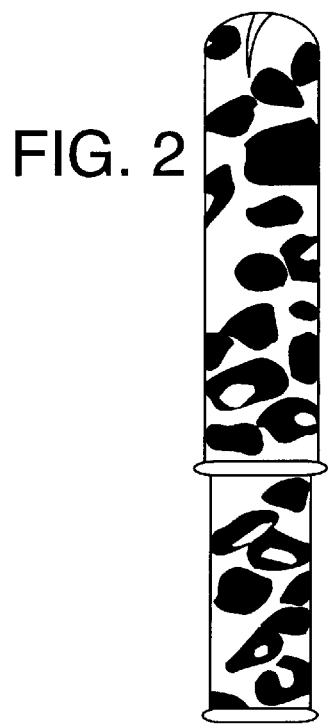
FIG. 2 is a view of a decorated tampon applicator and plunger.
Figure 3:
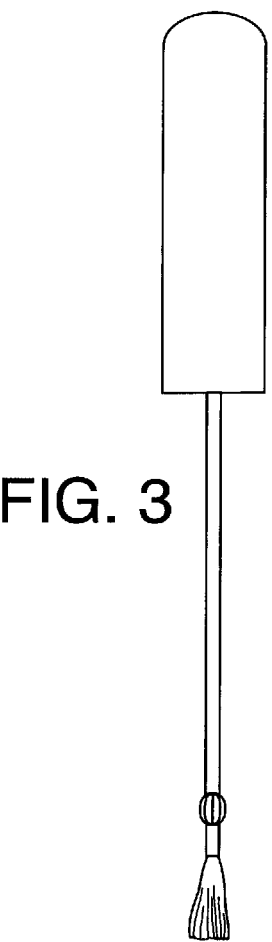
FIG. 3 is a view of the tampon pledget with a tasseled withdrawal string, the tassel comprising a cord, mold, skirt and ruff.
Figure 4:
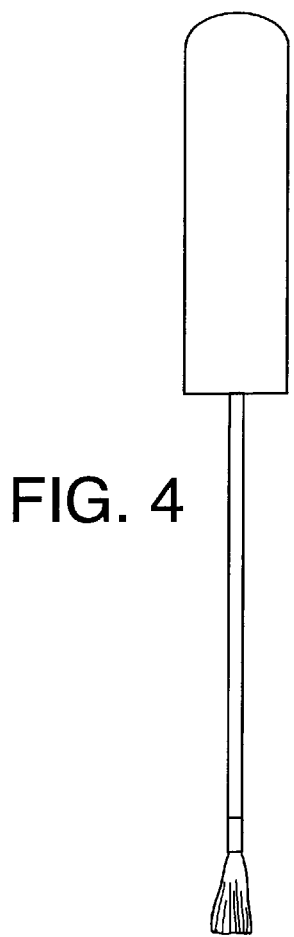
FIG. 4 is a view of the tampon pledget with a soft tassel withdrawal string with the cord bound directly to the skirt.

The following discussion describes in detail one embodiment of the invention and several variations of that embodiment. This discussion should not be construed, however, as limiting the invention to those particular embodiments. Practitioners skilled in the art will recognize numerous other embodiments as well.

A high-fashion designer tampon applicator and plunger may be intentionally ornamented with decorative patterns in any way known to those skilled in the visual and tactile arts.

Decorative patterns of the tampon applicator and plunger may include, but is not limited to, any full or partial combination of matching or contrasting colors, shades, fluorescents, metallics, patterns, designs, graphics, logos, flags or pictures. Decorative patterns of the tampon applicator and plunger may also include, but is not limited to any full or partial combination of matching or contrasting surface textures, finishes, applique, embossing, engraving, inscribing or molding. Decorative patterns may further include one or more animal prints, such as tiger, leopard or zebra skin.

Decorative patterns, coloring, or other ornamentation make the tampon applicator and plunger a high-fashion accessory rather than a "feminine hygiene" product. The decorative patterns on a designer tampon applicator and plunger can be likened to such ornamented fashion accessories such as hats, belts, purses, scarves or even jewelry. This decoration makes the designer tampon and plunger suitable for public display. Making the tampon applicator and plunger suitable for public display meets the objectives of removing embarrassment, eliminating stigma, and consequently raising the morale of the user.

Since the designer tampon applicator and plunger is intended for public display, eliminating the need for discretion will encourage the user to frequently change her tampon pledget. Encouraging frequent changes in tampon pledget decreases the risk of Toxic Shock Syndrome (TSS), a serious life-threatening infection.

Since the designer tampon applicator and plunger is intended for public display, it is not limited in size by the need for discretion. Removing the limitation in size meets the objective of allowing the designer tampon applicator to deliver a larger tampon pledget that is capable of providing a more adequate barrier and increased absorption of menstrual flow.

Given the designer tampon applicator and plunger are aesthetically pleasing in appearance, it can be expected to meet the objective of increasing compliance where a tampon is used for contraceptive, diagnostic, or therapeutic purposes. This is because a designer tampon is more pleasing, and less embarrassing to use, than a contraceptive, diagnostic, or therapeutic device. The designer tampon applicator and plunger makes a contraceptive, diagnostic, or therapeutic tampon more pleasing to use because it is a high fashion accessory suitable for public display. The designer tampon applicator and plunger makes a contraceptive, diagnostic, or therapeutic tampon less embarrassing to use because it diverts attention from purpose and towards appearance. The designer tampon applicator and plunger makes contraceptive, diagnostic and therapeutic tampons indistinguishable from catamenial tampons. The possibility of anonymous contraceptive, diagnostic or therapeutic use increases the probability of compliance.

The high-fashion designer withdrawal string may be made of a plurality of materials and intentionally decorated in any way known to those skilled in the art of passementerie. Passementerie is the art of making fringes, tassels and cords to embellish upholstery, soft furnishings and clothing.

A tassel is a decoration made of bunched loose threads, which are tied together at one end. Tassels typically comprise of four parts: the cord, the mold, the skirt and the ruff.

The function of the cord is to attach the tampon pledget to the tassel. A cord typically comprises of two, three or four strands of yarn spun in either a clockwise S twist or a counter-clockwise Z twist. Cords are then plied together in the opposite direction to create the thickness and visual effect desired. The cord or loop of cord is typically attached to the tassel by being threaded through the mold. However, a "soft tassel" can be made without a mold by attaching the cord to the skirt.

The mold is typically, but not necessarily, a turned wood shape with a central hole for the suspending cord. The maid may have a narrowed "waist" for external attachment of the fringed skirt. Alternatively the mold may be hollowed at one end for internal attachment of the fringed skirt. The mold may be made of any material known to those skilled in the art, such as plastic, ceramic, or glass. The mold may be decorated by horizontal rolling, vertical stripping, netting or snailing (trellising) with cord. Each technique can be applied alone or in combination to create the desired visual effect. As an alternative to covering with yarn, the mold may be painted or otherwise decorated in any way known to those skilled in the art. For example, where plastic is used for the mold, it may be colored in any way known to those skilled in the art. Where ceramic is used, it may be enameled in any way known to those skilled in the art. Where glass is used, it may be molded, cut or stained in any way known to those skilled in the art.

The skirt is the fringing which hangs down from a mold. There are two basic types of skirt: 1) a out skirt of loose yarn, or 2) a bullion skirt where the yarn twists back on itself in a folded loop. Each type of skirt may be used alone or in combination to create the desired visual effect. Alternatively, a squab skirt can be made by keeping the skirt short and tying it near the mid-point. The skirt may also be hung with Jasmines (four leaf flowers), drops of beads, pom-poms, tufts or other decorative devices known skilled in the art.

The ruff is a decorative device used to cover the joins where the different parts of the tassel meet. For example, a ruff may be applied where the cord meets the mold and where the mold meets the skirt.

In a "soft tassel" without a mold, binding, netting, or snailing, either alone or in combination, may be used to cover the joint between the cord and the skirt.

Intentional decoration of the withdrawal string may include, but is not limited to, a single tassel or multiple tassels consisting of but, not limited to, a single or looped cord, mold, skirt and ruff. The cord, which is attached at one end to the tampon pledget, may consist of a single or multiple strands, and each strand may be of a different material or color. The mold may be of a simple or complex design, and one or more molds may be threaded on the cord. In addition to or as an alternative to one or more molds, beads may be threaded along the cord. Rolling, striping, netting, and snailing, either alone or in any combination, may or may not be used to cover the mold or molds. As an alternative to covering with yarn, the mold may be painted or otherwise decorated. Where a material other than turned wood is used for the mold, it may be formed or decorated in any way appropriate to that material. In such case where no turned wood mold is used, knotting, binding, netting, snailing, or otherwise attaching the cord or cords directly to the skirt can make a "soft tassel". For example, the "mold"

may comprise of a knot, or the skirt may be trellised as a result of snailing, etc. The skirt may be a cut skirt, bullion skirt or combination skirt. The skirt may be made of the same or different material to cord. The skirt may be of matching or contrasting colors to the cord. The skirt may be a squab skirt. The skirt may or may not also include jasmines, drops of beads, pom-poms, tufts or other decorative devices.

A decorative tassel makes the withdrawal string a high-fashion accessory rather than a "feminine hygiene" product. The tasseled withdrawal string can be likened to such ornamented fashion accessories such as hats, belts, purses, scarves or even jewelry. The tasseled withdrawal string can be further likened to swimwear, sportswear or lingerie. The tasseled decoration makes the designer withdrawal string suitable for public display and personal or intimate adornment. Making the withdrawal string suitable for public display and personal or intimate adornment meets the objectives of removing embarrassment, eliminating stigma, and consequently raising the morale of the user.

A decorative tassel makes the withdrawal string highly visible. This meets the objective of providing a highly visible reminder to the user that a tampon is in place. Avoiding inadvertently leaving a tampon pledget in place decreases the risk of Toxic Shock Syndrome (TSS), a serious life-threatening infection.

A decorative tassel ensures that a withdrawal string has an adequate diameter and end stop. The cord provides an adequate diameter, and the mold, bead or "soft tassel" forms an adequate end stop. Together with the mold, bead or "soft tassel," the cord meets the objective of increasing the grip needed to facilitate removal of the tampon.

Given the tasseled designer withdrawal string is aesthetically pleasing in appearance, it can also be expected to meet the objective of increasing compliance where a tampon is used for contraceptive, diagnostic, or therapeutic purposes. This is because a tasseled designer withdrawal string is more pleasing, and less embarrassing to use, than a contraceptive, diagnostic, or therapeutic device. The tasseled designer withdrawal string makes a contraceptive, diagnostic, or therapeutic tampon more pleasing to use because it is a high fashion accessory intended for personal or intimate adornment. The tasseled designer withdrawal string makes a contraceptive, diagnostic, or therapeutic tampon less embarrassing to use because it diverts attention from the underlying purpose of the tampon by focusing attention on personal or intimate adornment. A designer withdrawal string makes, contraceptive, diagnostic and therapeutic tampons indistinguishable from catamenial tampons. The possibility of anonymous contraceptive, diagnostic or therapeutic use increases the probability of compliance.

It is anticipated that such a high-fashion designer tampon applicator, plunger and withdrawal string will be readily incorporated into coordinated sets of lingerie, sportswear, swimwear or other clothing.

What is claimed is:

1. A tampon applicator device comprising:
   (a) a tampon pledget;
   (b) an elongated tube capable of holding the tampon pledget, said tube having:
      i) an outer surface; and
      ii) first and second spaced apart ends;
   (c) a plunger having an outer periphery, said plunger being telescopically mounted in the first end of the tube; and
   (d) a tassel member extending from the tampon pledget, comprising:
      i) a cord member comprising at least one cord, said cord member having a first end and a second end, the first end being attached to the tampon pledget; and
      ii) a skirt extending from the second end of the cord member; and
   (e) a mold interposed between the cord member and the skirt.

2. The tampon applicator device of claim 1, wherein the mold is covered by rolling a fine cord thereon.

3. The tampon applicator device of claim 1, wherein the mold is covered with yarn.

4. The tampon applicator device of claim 1, wherein the mold is painted.

5. The tampon applicator device of claim 1, wherein the mold is a knot.

6. The tampon applicator device of claim 1, wherein the mold comprises one or more mold pieces being threaded along the cord.

7. A tampon applicator device comprising:
   (a) a tampon pledget;
   (b) an elongated tube capable of holding the tampon pledget, said tube having:
      i) an outer surface; and
      ii) first and second spaced apart ends;
   (c) a plunger having an outer periphery, said plunger being telescopically mounted in the first end of the tube; and
   (d) a tassel member extending from the tampon pledget, comprising:
      i) a cord member comprising at least one cord, said cord member having a first end and a second end, the first end being attached to the tampon pledget; and
      ii) a skirt extending from the second end of the cord member; and
   (e) a decorative pattern on the outer surface and the outer periphery; and
   (f) a mold interposed between the cord member and the skirt.

8. The tampon applicator device of claim 7, wherein the mold is covered by rolling a fine cord thereon.

9. The tampon applicator device of claim 7, wherein the mold is covered with yarn.

10. The tampon applicator device of claim 7, wherein the mold is painted.

11. The tampon applicator device of claim 7, wherein the mold is a knot.

12. The tampon applicator device of claim 7, wherein the mold comprises one or more mold pieces being threaded along the cord.

* * * * *

(12) SUPPLEMENTAL EXAMINATION CERTIFICATE

United States Patent
Bernard

(10) Number: 6,676,625 F1
(45) Certificate Issued: Aug. 3, 2020

Control No.: 96/000,329

Filing Date: Jun. 19, 2020

Primary Examiner: Cary E. Wehner

No substantial new question of patentability is raised in the request for supplemental examination. See the Reasons for Substantial New Question of Patentability Determination in the file of this proceeding.

(56) Items of Information

U.S. PATENT DOCUMENTS

| | | |
|---|---|---|
| 2,934,068 | 4/1960 | Graham, Jr., et al. |
| 3,762,413 | 10/1973 | Hanke |
| 4,857,044 | 8/1989 | Lennon |
| 5,395,308 | 3/1995 | Fox et al. |
| 5,873,971 | 2/1999 | Balzar |
| 6,045,526 | 4/2000 | Jackson |
| 6,142,984 | 11/2000 | Brown et al. |
| 6,312,419 | 11/2001 | Durel-Crain |
| 6,599,279 | 7/2003 | Taylor et al. |
| 5,569,177 | 10/1996 | Fox et al. |

FOREIGN PATENT DOCUMENTS

| | | |
|---|---|---|
| WO | 00/72792 A1 | 12/2000 |